United States Patent
Wrolstad et al.

(10) Patent No.: US 11,857,362 B2
(45) Date of Patent: *Jan. 2, 2024

(54) IMAGING ASSEMBLY FOR INTRAVASCULAR IMAGING DEVICE AND ASSOCIATED DEVICES, SYSTEMS, AND METHODS

(71) Applicant: PHILIPS IMAGE GUIDED THERAPY CORPORATION, San Diego, CA (US)

(72) Inventors: David Kenneth Wrolstad, Fallbrook, CA (US); Maritess Minas, San Diego, CA (US); Princeton Saroha, Ladera Ranch, CA (US); Jeremy Stigall, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 17/514,943

(22) Filed: Oct. 29, 2021

(65) Prior Publication Data

US 2022/0047242 A1 Feb. 17, 2022

Related U.S. Application Data

(63) Continuation of application No. 16/088,280, filed as application No. PCT/IB2017/051727 on Mar. 27, 2017, now Pat. No. 11,160,529.

(Continued)

(51) Int. Cl.
*A61B 8/00* (2006.01)
*A61B 8/12* (2006.01)
*H05K 1/18* (2006.01)

(52) U.S. Cl.
CPC .............. *A61B 8/12* (2013.01); *A61B 8/4483* (2013.01); *H05K 1/189* (2013.01)

(58) Field of Classification Search
CPC combination set(s) only.
See application file for complete search history.

(56) References Cited

U.S. PATENT DOCUMENTS

| 6,776,763 B2 | 8/2004 | Nix |
| 7,226,417 B1 | 6/2007 | Eberle |
| 11,160,529 B2 * | 11/2021 | Wrolstad ............. A61B 8/4483 |

FOREIGN PATENT DOCUMENTS

EP 0853919 A2 7/1998

* cited by examiner

*Primary Examiner* — Joel Lamprecht

(57) ABSTRACT

A method of assembling an intravascular imaging device is provided. In one embodiment, the method includes obtaining a support member having a body portion including a plurality of recesses longitudinally spaced from one another; positioning a flex circuit around the support member such that the flex circuit is radially spaced from the body portion of the support member; and filling a space between the flex circuit and the support member with a backing material through the plurality of recesses of the body portion. In one embodiment, an intravascular imaging device includes a flexible elongate member; an imaging assembly including: a flex circuit; and a support member around which the flex circuit is disposed, the support member having a body portion including plurality of recesses, wherein the support member defines lumen in fluid communication with a space between the flex circuit and the support member via the plurality of recesses.

12 Claims, 19 Drawing Sheets

Related U.S. Application Data

(60) Provisional application No. 62/315,428, filed on Mar. 30, 2016.

IMAGING ASSEMBLY FOR INTRAVASCULAR IMAGING DEVICE AND ASSOCIATED DEVICES, SYSTEMS, AND METHODS

CROSS-REFERENCE TO RELATED APPLICATIONS

This application is a continuation of U.S. application Ser. No. 16/088,280, filed Sep. 25, 2018, now U.S. Pat. No. 11,160,529, which is the U.S. National Phase application under 35 U.S.C. § 371 of International Application No. PCT/IB2017/051727, filed on Mar. 27, 2017, which claims the benefit of Provisional Application Ser. No. 62/315,428, filed Mar. 30, 2016. These applications are hereby incorporated by reference herein.

TECHNICAL FIELD

The present disclosure relates generally to intravascular ultrasound (IVUS) imaging and, in particular, to the structure of an intravascular imaging device. For example, the intravascular imaging device can include an imaging assembly at a distal portion thereof having a support member and a flex circuit positioned around the support member.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse physiology within the human body is challenging. In that regard, components at the distal portion of the imaging device can be assembled in a manner that excessively enlarges an outer diameter, which makes navigation through smaller diameter vessels difficult. Ensuring robust mechanical coupling between components can also be challenging.

Thus, there remains a need for intravascular ultrasound imaging system that overcomes the limitations of a large diameter imaging assembly while achieving strong and efficient assembly and operation.

SUMMARY

Embodiments of the present disclosure provide an improved intravascular ultrasound imaging system for generating images of a blood vessel. A distal portion of an intravascular imaging device can include a flex circuit and a support member around which the flex circuit is positioned. The support member can include longitudinally spaced recesses. A space between the flex circuit and the support member can be filled with an acoustic backing material that is introduced via the recesses. The flex circuit can include a conductor interface that extends at an oblique angle relative to a main body of the flex circuit. The conductor interface can advantageously allow for conductors to the electrically coupled to the flex circuit while minimizing outer diameter. Lap joints can be used to join flex circuit and proximal and distal members, which provide strong connections between components. A proximal portion of the support member can include cavities that allow for adhesive to effectively bind components at the proximal portion of the imaging assembly In one embodiment, a method of assembling an intravascular imaging device is provided. The method includes obtaining a support member having a body portion including a plurality of recesses longitudinally spaced from one another; positioning a flex circuit around the support member such that the flex circuit is radially spaced from the body portion of the support member; and filling a space between the flex circuit and the support member with a backing material through the plurality of recesses of the body portion.

In some embodiments, the support member defines lumen in fluid communication with the space between the flex circuit and the support member via the plurality of recesses. In some embodiments, the filling includes introducing the backing material into the lumen of the support member such that the backing material flows into the space between the space between the flex circuit and the support member via the plurality of recesses. In some embodiments, the method further includes positioning a mandrel within the lumen before filing the space between the flex circuit and the support member with the blacking material; and removing the mandrel after the backing material cures. In some embodiments, the method further includes removing excess backing material from the lumen after the backing material cures. In some embodiments, each of the plurality of recesses extends from an outer surface of body portion through an inner surface of the lumen. In some embodiments, the body portion of the support member surrounds the lumen. In some embodiments, the support member includes proximal and distal stands, the body portion extending longitudinally between the proximal and distal stands, and wherein the proximal and distal stands have a larger outer diameter than the body portion. In some embodiments, the positioning a flex circuit around the support member includes wrapping the flex circuit in a cylindrical configuration around the support member such that the flex circuit is in contact with the proximal and distal stands and spaced from the body portion of support member. In some embodiments, the method further includes evacuating air from the space between the flex circuit and the support member via an opening in at least one of the proximal or distal stands.

In some embodiments, the method further includes coupling a distal member to at least one of the flex circuit or the support member. In some embodiments, the flex circuit and the distal member form a lap joint. In some embodiments, the support member includes a distal flange sized and shaped to facilitate coupling to the distal member. In some embodiments, the method further includes coupling a proximal member to at least one of the flex circuit or the support member. In some embodiments, the flex circuit and the distal member form a lap joint. In some embodiments, the support member includes a proximal flange having a plurality of cavities, and wherein the coupling a proximal member comprises: applying an adhesive to affix the proximal member and the support member; curing the adhesive with light delivered to the adhesive via the plurality of cavities of the proximal flange. In some embodiments, the flex circuit comprises a conductor interface extending at an oblique angle relative to a body of the flex circuit, and wherein the method further comprises electrically coupling a conductor to the conductor interface. In some embodiments, the method further includes positioning the conductor interface around a proximal flange of the support member such that the conductor is electrically coupled to the conductor interface spaced from the main body of the flex circuit. In some embodiments, the conductor interface is spirally wrapped around the proximal flange.

In one embodiment, an intravascular imaging device is provided. The intravascular imaging device includes a flexible elongate member sized and shaped for insertion into a vessel of a patient, the flexible elongate member having a proximal portion and a distal portion; an imaging assembly disposed at the distal portion of the flexible elongate member, the imaging assembly including: a flex circuit; and a support member around which the flex circuit is disposed, the support member having a body portion including plurality of recesses, wherein the support member defines lumen in fluid communication with a space between the flex circuit and the support member via the plurality of recesses.

In some embodiments, the support member further comprises proximal and distal stands having a larger outer diameter than the body portion, the body portion extending longitudinally between the proximal and distal stands; and the flex circuit is in contact with the proximal and distal stands and spaced from the body portion of support member. In some embodiments, the device further includes a backing material disposed in the space between the flex circuit and the support member. In some embodiments, the device further includes a distal member coupled to at least one of the flex circuit or the support member, wherein the flex circuit and the distal member form a lap joint. In some embodiments, the support member comprises a distal flange sized and shaped to facilitate coupling to the distal member. In some embodiments, the device further includes a proximal member coupled to at least one of the flex circuit or the support member, wherein the flex circuit and the distal member form a lap joint. In some embodiments, the device further includes a plurality of conductors extending along the flexible elongate member, wherein flex circuit comprises a conductor interface extending at an oblique angle relative to a body of the flex circuit, and wherein the plurality of conductors electrically coupled to the conductor interface. In some embodiments, the support member further comprises a proximal flange, wherein the conductor interface is positioned around the proximal flange such that the conductor is electrically coupled to the conductor interface spaced from the main body of the flex circuit. In some embodiments, the conductor interface is spirally wrapped around the proximal flange.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
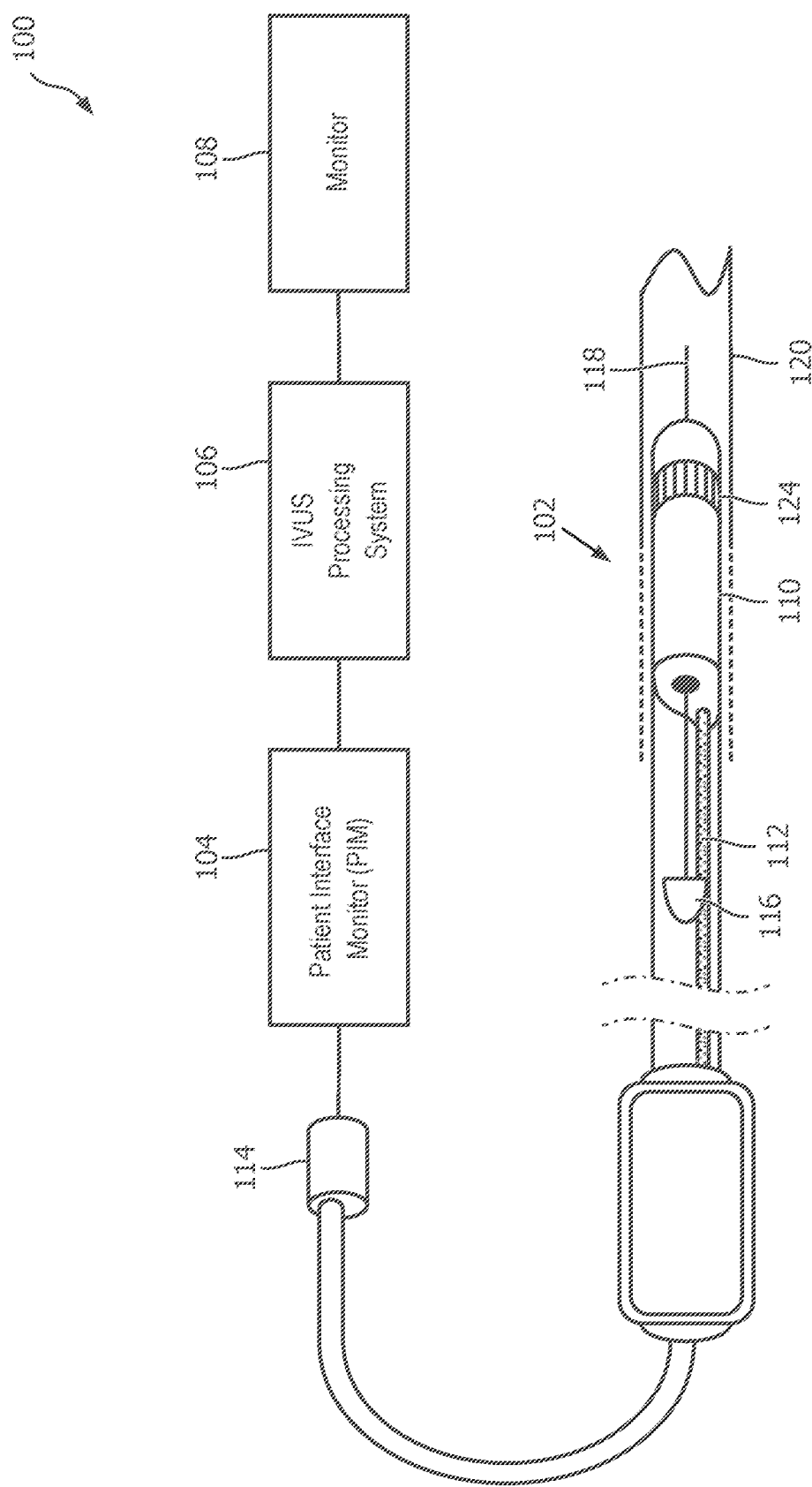
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
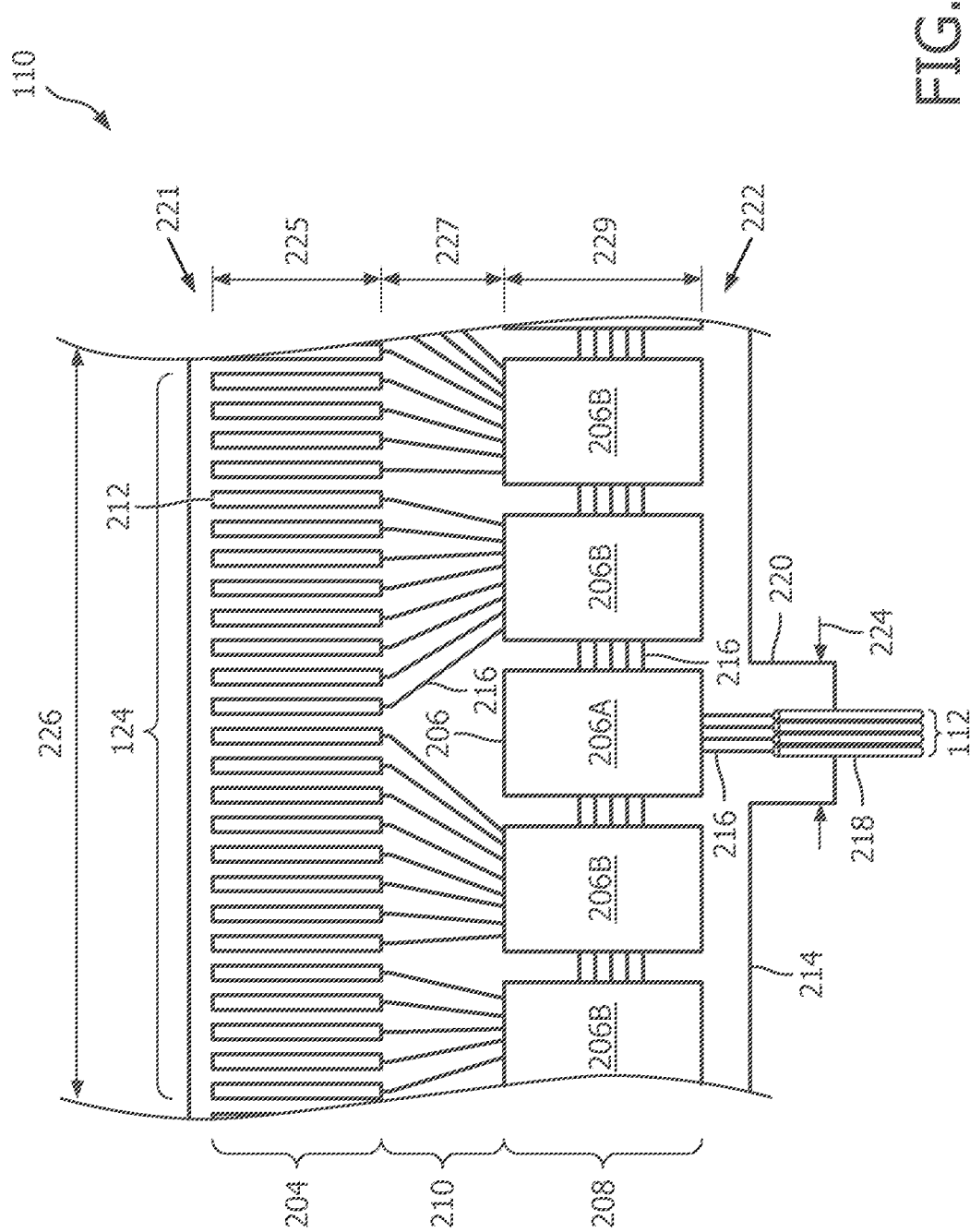
FIG. 2 is a diagrammatic top view of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

Figure 3:
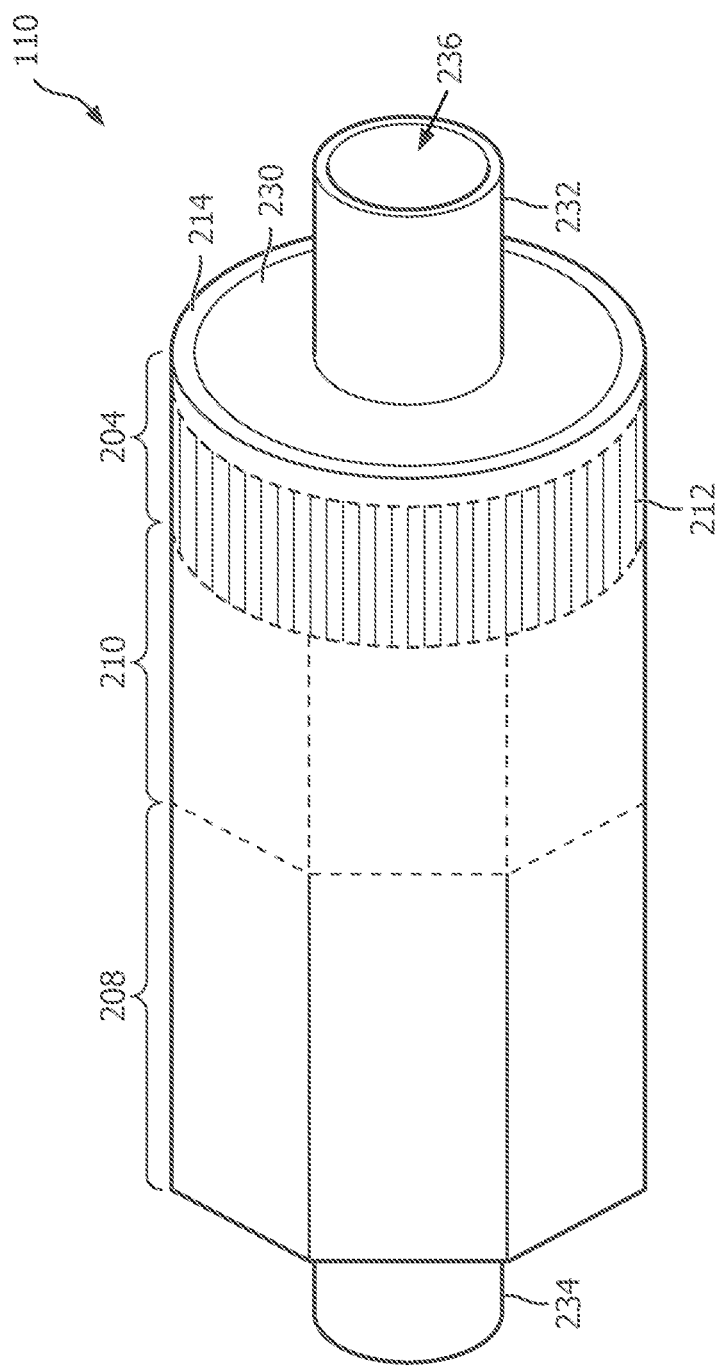
FIG. 3 is a diagrammatic side view of a scanner assembly in a rolled configuration around a support member, according to aspects of the present disclosure.

FIG. 2 is a top view of a portion of an ultrasound scanner assembly 110 according to an embodiment of the present disclosure. The assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flex circuit 214 that is shown in a flat configuration in FIG. 2. FIG. 3 illustrates a rolled configuration of the flex circuit 214. The transducer array 202 is a non-limiting example of a medical sensor element and/or a medical sensor element array. The transducer control logic dies 206 is a non-limiting example of a control circuit. The transducer region 204 is disposed adjacent a distal portion 221 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the imaging assembly 110 is described as including a flex circuit, it is understood that the transducers and/or controllers may be arranged to form the imaging assembly 110 in other configurations, including those omitting a flex circuit.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 124 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON' (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 μm and 100 μm, with some particular embodiments being between 12.7 μm and 25.1 μm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 μm. For example, in an embodiment, 20 μm conductive traces 216 are separated by 20 μm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 114 are coupled to the flex circuit 214. For example, the bare conductors of the cable 114 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 220, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 220 and/or the conductor(s) 218 can be variously configured to facilitate efficient manufacturing and operation of the scanner assembly 110.

Figure 4:
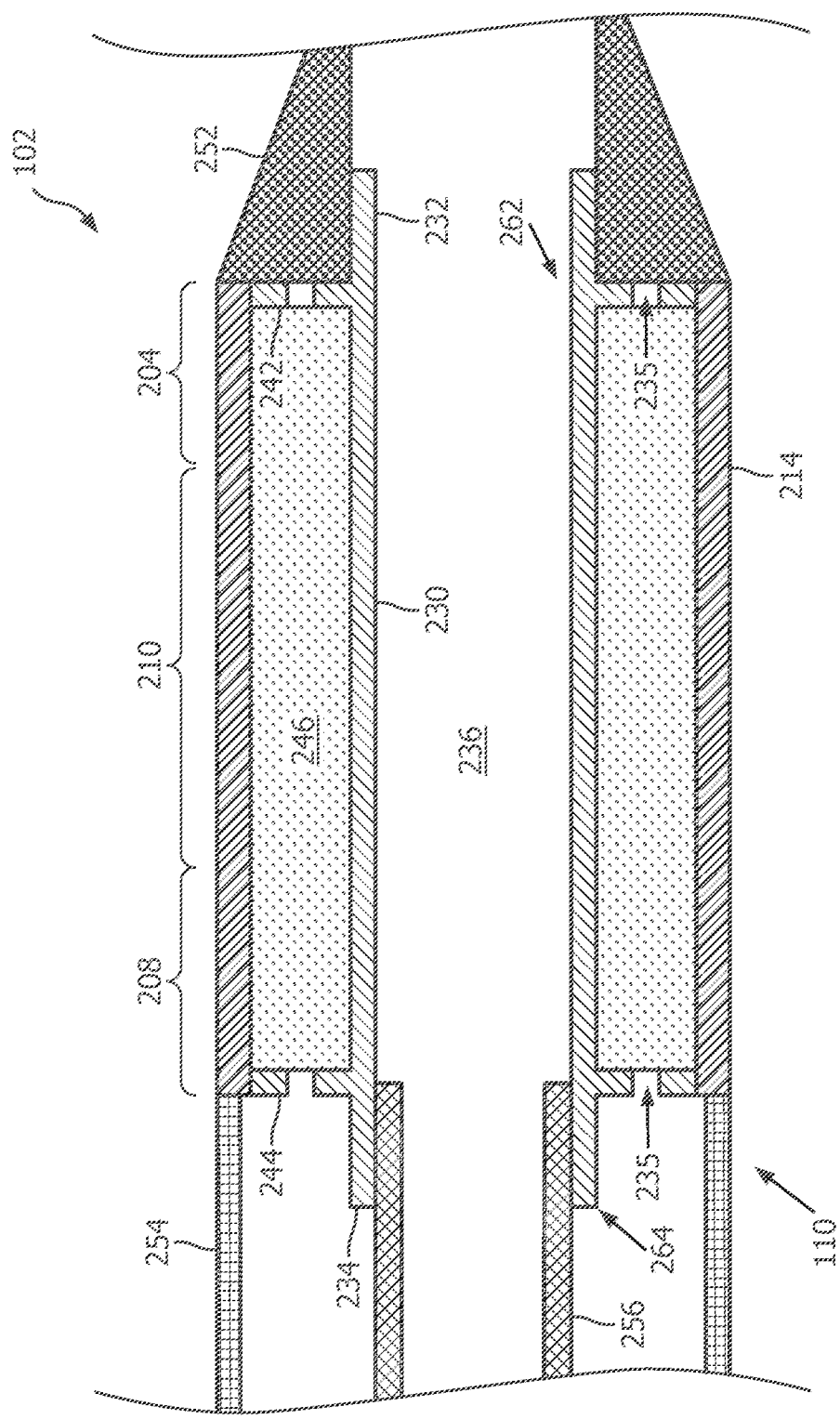
FIG. 4 is a diagrammatic cross-sectional side view of a distal portion of an intravascular device, according to aspects of the present disclosure.

In some instances, the scanner assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view with the flex circuit 214 in the rolled configuration around the support member 230, according to aspects of the present disclosure. FIG. 4 is a diagrammatic cross-sectional side view of a distal portion of the intravascular device 110, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another.

Stands 242, 244 that extend vertically are provided at the distal and proximal portions 262, 264, respectively, of the support member 230. The stands 242, 244 elevate and support the distal and proximal portions of the flex circuit 214. In that regard, portions of the flex circuit 214, such as the transducer portion 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244. To improve acoustic performance, any cavities between the flex circuit 214 and the surface of the support member 230 are filled with a backing material 246. The liquid backing material 246 can be introduced between the flex circuit 214 and the support member 230 via passageways 235 in the stands 242, 244. In some embodiments, suction can be applied via the passageways 235 of one of the stands 242, 244, while the liquid backing material 246 is fed between the flex circuit 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be flexible elongate member that extend from proximal portion of the intravascular 102, such as the proximal connector 114, to the imaging assembly 110. For example, the proximal inner member 256 can be received within a proximal flange 234. The proximal outer member 254 abuts and is in contact with the flex circuit 214. A distal member 252 is coupled to the distal portion 262 of the support member 230. The distal member 252 can be a flexible component that defines a distal most portion of the intravascular device 102. For example, the distal member 252 is positioned around the distal flange 232. The distal member 252 can abut and be in contact with the flex circuit 214 and the stand 242. The distal member 252 can be the distal-most component of the intravascular device 102.

One or more adhesives can be disposed between various components at the distal portion of the intravascular device 102. For example, one or more of the flex circuit 214, the support member 230, the distal member 252, the proximal inner member 256, and/or the proximal outer member 254 can be coupled to one another via an adhesive.

Figure 5:
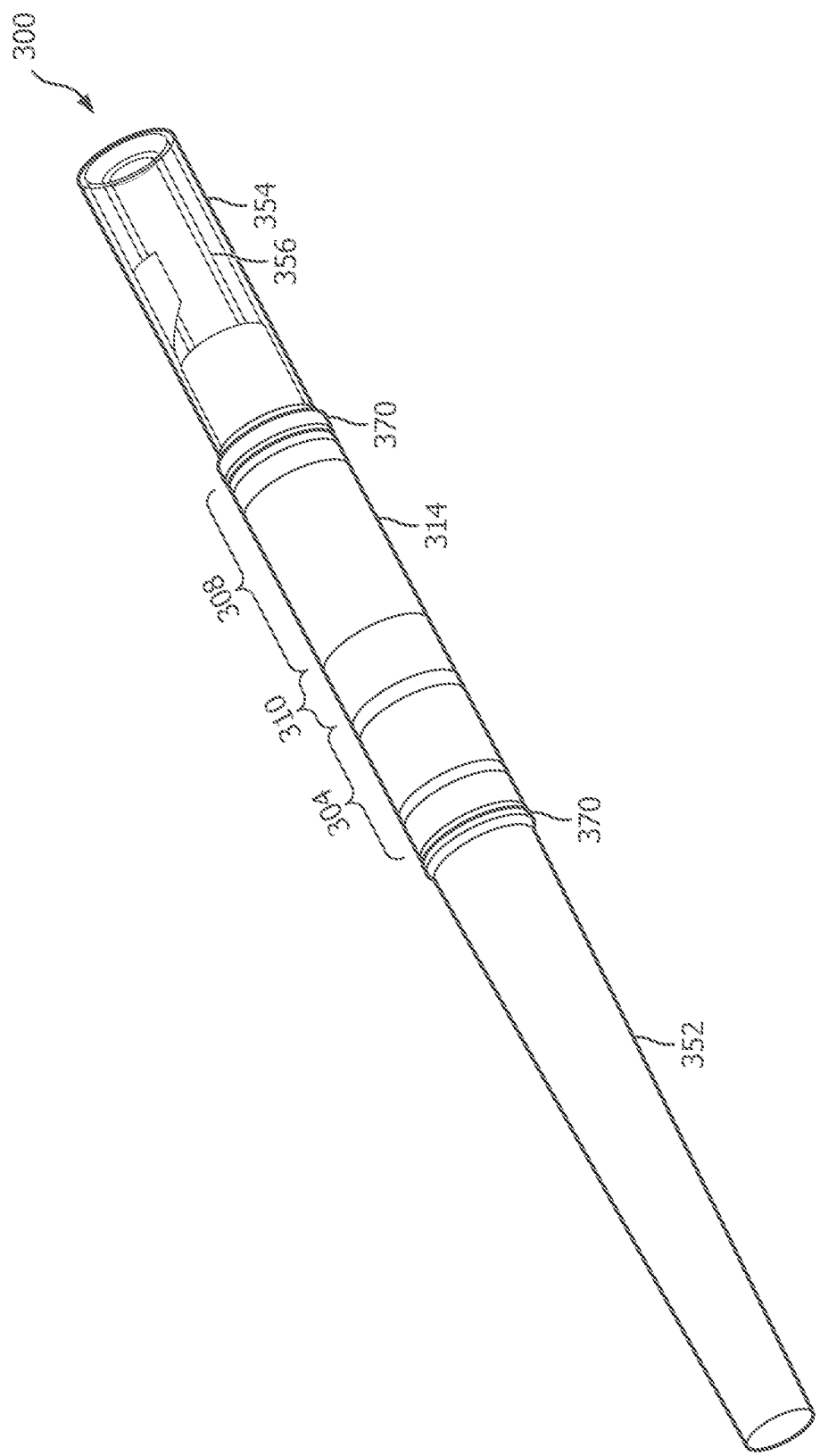
FIG. 5 is a side view illustration of the intravascular device, according to aspects of the present disclosure.
Figure 6:
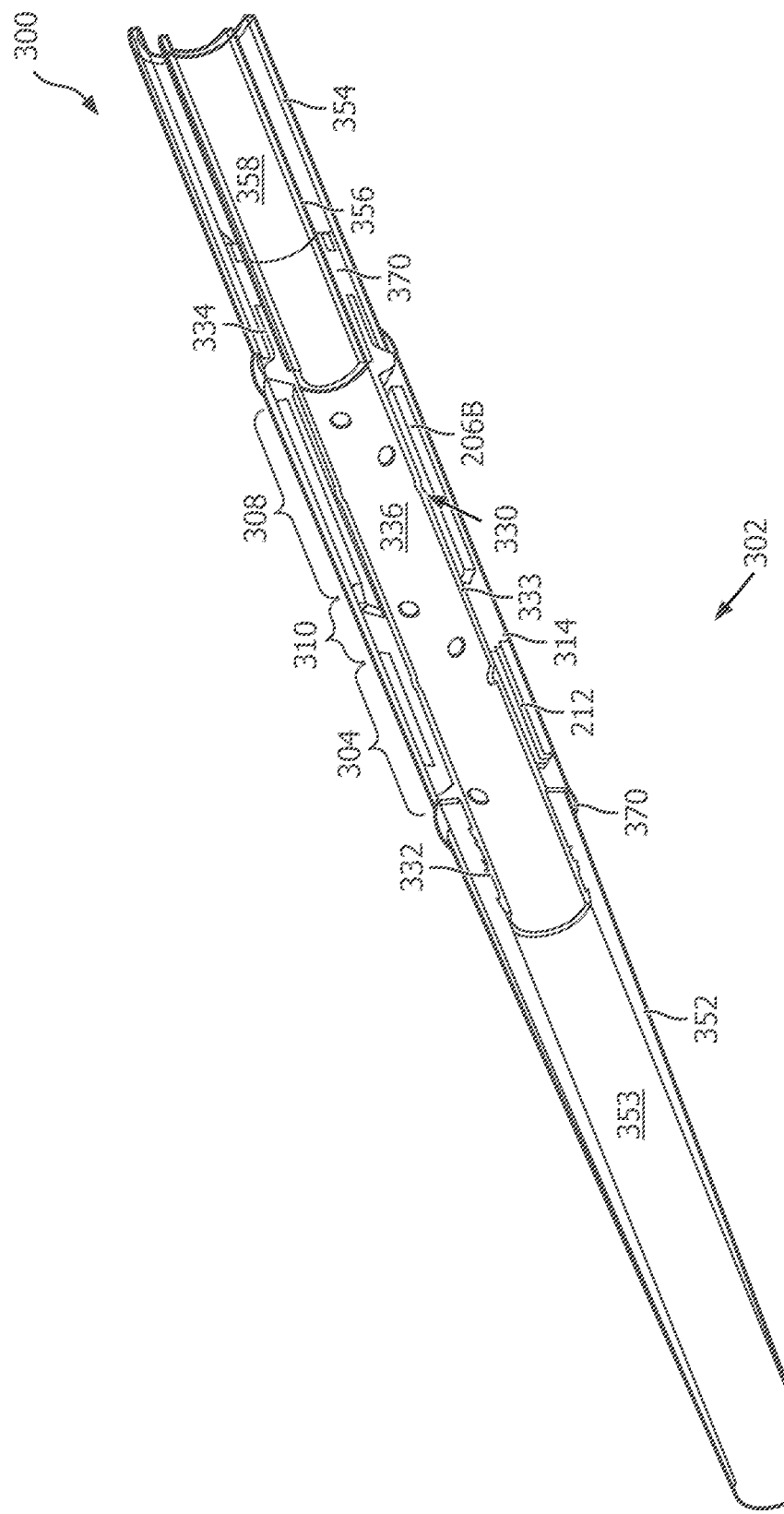
FIG. 6 is a cross-sectional side view illustration of the intravascular device of FIG. 5.

FIGS. 5 and 6 illustrate an embodiment of an intravascular device 300, including an imaging assembly 302. FIG. 5 is a side view illustration of the intravascular device 300. FIG. 6 is cross-sectional side view illustration of the intravascular device 300. For clarity, the distal portion of the intravascular device 300 is shown the left side of FIGS. 5 and 6, and more proximal portions are shown on the right side.

The intravascular device 300 and the imaging assembly 302 can be similar the intravascular device 102 and the imagine assembly 110, respectively, in some aspects. The imaging assembly 302 is disposed at a distal portion of the intravascular device 300. The imaging assembly 302 includes a flex circuit 314 having a transducer region 304 with a plurality of transducers 212, a controller region 308 having a plurality of controllers, including the controller(s) 206B, and a transition region 310 having a plurality of conductive traces facilitating electrical communication between the controllers 206A, 206B and the transducers 212.

The flex circuit 314 is positioned around the support member 330 having a distal flange 332, a body portion 333, and a proximal flange 334. The support member 330 defines a longitudinal lumen 336 that is sized and shaped to receive the guide wire 118. The flex circuit 314 is positioned in a rolled, cylindrical, and/or cylindrical toroid manner around the support member 330.

A distal member 352 extends distally from the support member 330 and is positioned around the distal flange 332. The distal member 352 defines a lumen 353 sized and shaped to receive the guide wire 118 and in communication with the lumen 336 of support member 330. The distal member 352 may be mechanically coupled to the flex circuit 314 and/or the support member 330 via adhesive 370.

One or more proximal members 354, 356 extend proximally from the support member 330. For example, an outer member 354 may be positioned around the proximal flange 334, and the inner member 356 may be received within the proximal flange 334. The inner member 356 may define a lumen 358 sized and shaped to receive the guide wire 118 and in communication with the lumen 336. The one or more proximal members 354, 356 may be mechanically coupled to the flex circuit 314 and/or the support member 330 via adhesive 370.

Figure 7:
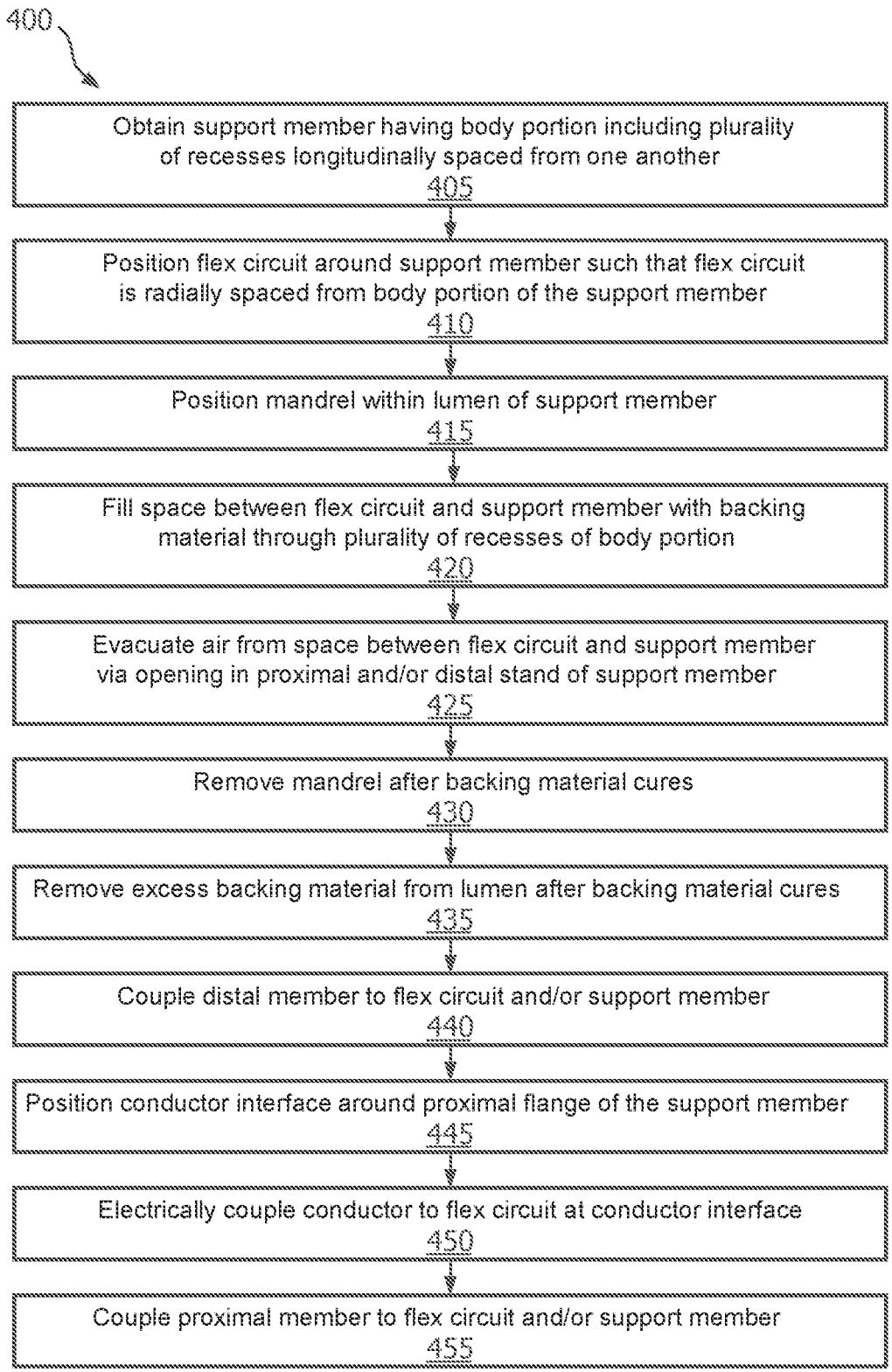
FIG. 7 is a flow diagram of a method of assembling an intravascular imaging device, according to aspects of the present disclosure.

FIG. 7 is a flow diagram of a method 400 of assembling an intravascular imaging device, including an imaging assembly with a support member described herein. It is understood that the steps of method 400 may be performed in a different order than shown in FIG. 7, additional steps can be provided before, during, and after the steps, and/or some of the steps described can be replaced or eliminated in other embodiments. The steps of the method 400 can be carried out by a manufacturer of the intravascular imaging device.

At step 405, the method 400 includes obtaining a support member. The support member includes a body portion having a plurality of recesses longitudinally spaced from one another. The body portion can extend between proximal and distal stands that have a larger outer diameter than the body portion. The support member defines longitudinal lumen extending therethrough. The body portion surrounds the lumen. Each of the plurality of longitudinally-spaced recesses extends from an outer surface of body portion through to an inner surface of the lumen.

At step 410, the method 400 includes positioning a flex circuit around the support member. The flex circuit includes a first section having a plurality of transducers, a second section having a plurality of controllers, and a third section having a plurality of conductive traces facilitating communication between the plurality of the transducers and the plurality of controllers. The flex circuit can be wrapped in a cylindrical configuration around the support member. The flex circuit can be radially spaced from the body portion when positioned around the support member. For example, proximal and distal portions of the flex circuit are in contact with the proximal and distal stands, respectively. A central portion of the flex circuit, between the proximal and distal portions, is radially spaced from the body portion of support member. Adhesive or other coupling mechanism may be used to join the flex circuit and the support member.

At step 415, the method 400 may include positioning a mandrel with the lumen of the support member. The mandrel may stabilize the support member during assembly of the intravascular device. In some embodiments, the mandrel may be coated and/or otherwise covered with a lubricous material, such as TEFLON® (registered trademark of E.I. du Pont) and/or other suitable material.

The method 400 may additionally include positioning a plug within the lumen defined by the support member. For example, the plug may be positioned at a proximal portion of the lumen when backing material directed into the lumen from the distal portion, and the plug may be positioned at a distal portion of the lumen when backing material directed into the lumen from the distal portion, as described with respect to step 420.

At step 420, the method 400 includes filling a space between the flex circuit and the support member with a backing material. In that regard, the space between the flex circuit and support member is created when the flex circuit is positioned around the support member. In particular, the central portion of flex circuit is radially spaced from the body portion of the support member because the proximal and distal portions of the flex circuit contact the larger diameter stands of the support member, when the flex circuit is wrapped or rolled around the support member. The backing material may be an acoustic backing material that facilitates operation of the transducers. The backing material may be liquid when introduced into the space between the flex circuit and the support member. The lumen defined by the support member may be in fluid communication with the space between the flex circuit and the support member via the plurality of recesses of the support member. Accordingly, step 420 can include introducing the backing material into the lumen of the support member such that the backing material flows into the space between the space between the flex circuit and the support member via the plurality of recesses. In some embodiments, the backing material may be introduced in substantially equal proportions along the longitudinal length of the support member lumen. The recesses of the body portion of the support member may be axially/longitudinally and/or circumferentially distributed to allow the backing material to evenly fill the longitudinally length of the space between the flex circuit and the support member. In some embodiments, backing material may be directed into the lumen through the lumen opening at the proximal portion or the distal portion such that backing material flows into the space between the support member and the flex circuit via the plurality of recesses. In some embodiments, a conduit may be inserted at least partially into the lumen and the backing material may be directed into the lumen and/or the space between the support member and the flex circuit.

At step 425, the method 400 can include evacuating air from the space between the flex circuit and the support member. This may advantageously prevent uneven filling/distribution of the backing material within the space because of air pockets. Air may be evacuated from the space by applying suction at one or more openings in the proximal stand and/or distal stand of the support member. Steps 420 and 425 may be performed simultaneously to efficiently fill the space between the flex circuit and the support member with the backing material.

At step 430, the method 400 includes removing the mandrel from the support member lumen after backing material cures. Because the mandrel may be coated with a lubricous material, the mandrel may be quickly and easily removed from the lumen.

At step 435, the method 400 includes removing excess backing material from the support member lumen after the backing material cures. Because the liquid backing material was introduced into the space between the flex circuit and the support member through the lumen, the lumen may include excess backing material. Step 435 may including reaming the support member lumen to remove the excess backing material which ensures that the internal diameter of the support member lumen is available to receive a guide wire. Removing the excess backing material may include sliding a component having a diameter equal to or slight less than the diameter of the support member lumen through the lumen. The exertion of the component against the excess backing material within the lumen clears the lumen of the excess backing material. The component also removes the plug which may be positioned at a proximal or distal portion of the lumen. The component used to remove the excess backing material may be formed of a material, such as polytetrafluoroethylene (PTFE) or TEFLON® (registered trademark of E.I. du Pont) and/or other suitable material, through the lumen.

The acoustic backing material cures over time. Light and/or heat may be applied in some instances to cure the backing material.

At step 440, the method 400 includes coupling a distal member to the flex circuit and/or the support member. The support member may include a distal flange that is sized and shaped to facilitate coupling to the distal member. When joined, a distal portion of the flex circuit may extend over a proximal portion of the distal member such that the flex circuit and the distal member form a lap joint. Adhesive may be positioned between the distal member, the flex circuit, and/or the support member to affix the components.

At step 450, the method 400 includes electrically coupling one or more conductors to the flex circuit. For example, the flex circuit may include a conductor interface that extends at an oblique angle relative to a body of the flex circuit. The conductive traces of the conductor interface are in electrical communication with electronic components of the flex circuit, such as the controllers, transducers, and/or other conductive traces. Electrically coupling the one or more conductors establishes electrical communication between the conductors and the components of the flex circuit. For example, the conductors can be soldered to the conductor interface. The conductor interface can extend from the main body of the flex circuit such that the location on the conductor interface where the conductors are soldered is advantageously spaced from the main body of the flex circuit. For example, the conductor interface can be positioned around, such as in a spiral and/or other suitable configuration, around a proximal flange of the support member. The outer diameter of the intravascular device can be advantageously minimized by connecting the conductor to the conductor interface of the flex circuit spaced from the controllers and/or transducers of the flex circuit.

At step 455, the method 400 includes coupling one or proximal members to the flex circuit and/or the support member. For example, an inner member and/or an outer member can be coupled to the flex circuit and/or the support member. In some embodiments, the inner member and outer member can be coupled to the flex circuit and/or the support member at different steps of the method 400. The support member may include a proximal flange that is sized and shaped to facilitate coupling to the proximal member(s). For example, the proximal flange may have a plurality of cavities that extends radially inwards from an outer surface of the proximal flange through the inner wall of the support member lumen. The inner proximal member may be positioned within the proximal flange. Step 455 can include applying adhesive to affix the inner proximal member and the support member. The adhesive may also adhere to the conductor interface that is positioned around the proximal flange. Light and/or heat may be delivered to the adhesive via the plurality of cavities in the proximal flange to allow curing of the adhesive. The outer proximal member may be positioned around the proximal flange. When joined, a proximal portion of the flex circuit may extend over a distal portion of the outer proximal member such that the flex circuit and the outer proximal member form a lap joint. Adhesive may be positioned between the one or more distal members, the flex circuit, and/or the support member to affix the components.

Figure 8:
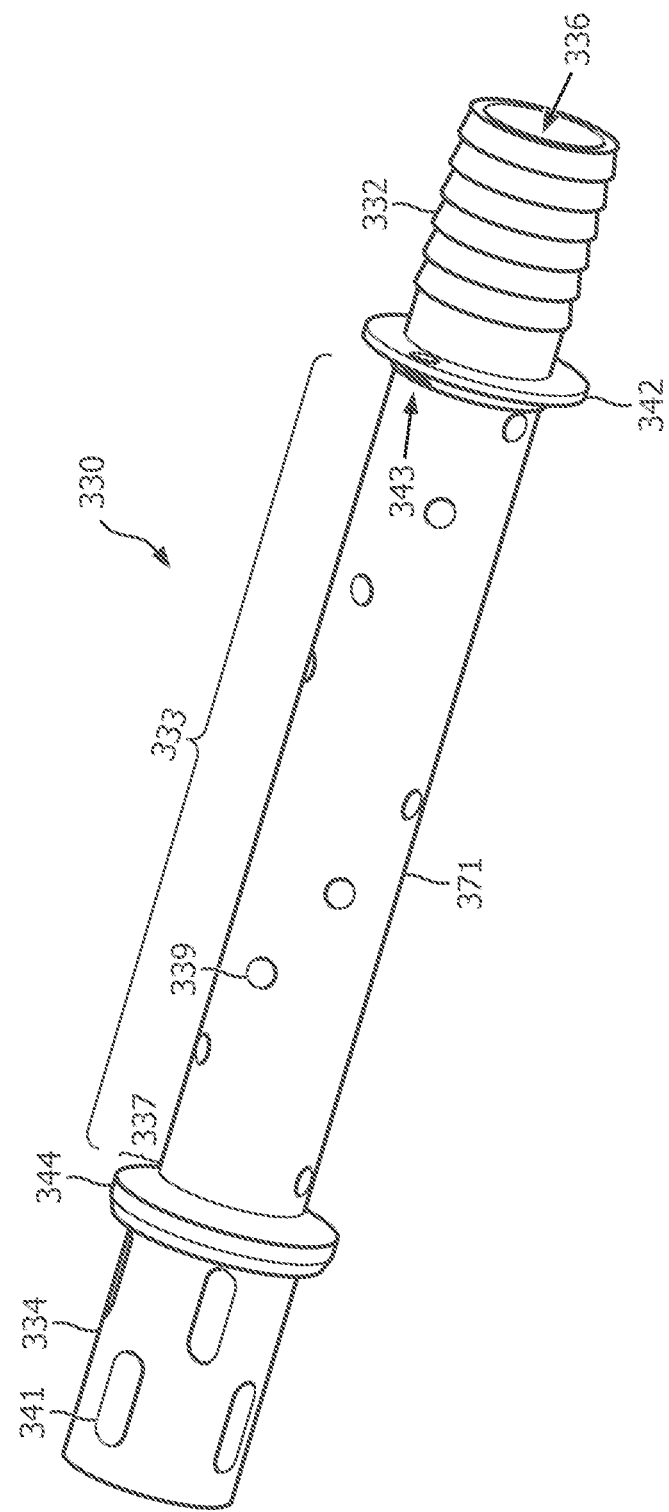
FIG. 8 is a perspective view illustration of a support member, according to aspects of the present disclosure.

FIG. 8 is perspective view illustration of an embodiment of the support member 330. The support member 330 is described with reference also to FIG. 10, which is a cross-sectional side view illustration of a distal portion of the intravascular device 300, including the support member 330. The support member 330 may be metallic or non-metallic in various embodiments. For example, the support member 330 may be molded plastic or polymer.

The support member 330 includes the body portion 333 extending between the distal stand 342 and the proximal stand 344. The proximal and distal stands 342, 344 have a larger outer diameter than the body portion 333. The larger outer diameter of the proximal and distal stands 342, 344 define a radial space 337. As described herein, when the flex circuit 314 is positioned around the support member 330, the space 337 can be filed with the acoustic backing material. In that regard, the body portion 333 includes multiple recesses or holes 339 that are spaced from one another. The recesses 339 may be longitudinally and/or circumferentially distributed on the body portion 333. In that regard, the recesses 339 may be arranged in any suitable distribution or pattern along the body portion 333. In the illustrated embodiments, the recesses 339 may form two spirals around the body portion 333. It is understand any suitable pattern of recesses 339, including one, two, three, four, or more spirals, a geometric pattern, such as a checkerboard, or other regularly spaced pattern, irregular pattern, random pattern, and/or other suitable distribution may be utilized. Each of the recesses 339 extends radially from an outer surface 371 of the support member through an inner wall 372 of the lumen 336. The recesses 339 establish fluid communication between the lumen 336 extending longitudinally through the support member and the space 337. The space 337 may be filled with the acoustic backing material by introducing the backing material into the lumen such that the backing material flows in the space 337 through the recesses 339. In that regard, the recesses 339 may be distributed and/or spaced from one another such that the backing material evenly fills the space 337. Recesses 339 may have any suitable shape, including a circle (as shown), polygon, ellipse, etc.

In the illustrated embodiment, the stand 342 includes an opening 343. The opening 343 extends longitudinally between proximal and distal sides of the stand 342. When the space 337 is filled with the backing material, suction may be applied at the opening 343 to evacuate any air in the space 337. While only one opening 343 is shown, it is understood more than one opening 343 may be provided on the stand 342. In other embodiments, opening(s) 343 may be provided only on the proximal stand 344 and/or both the proximal and distal stands 342, 344.

Figure 10:
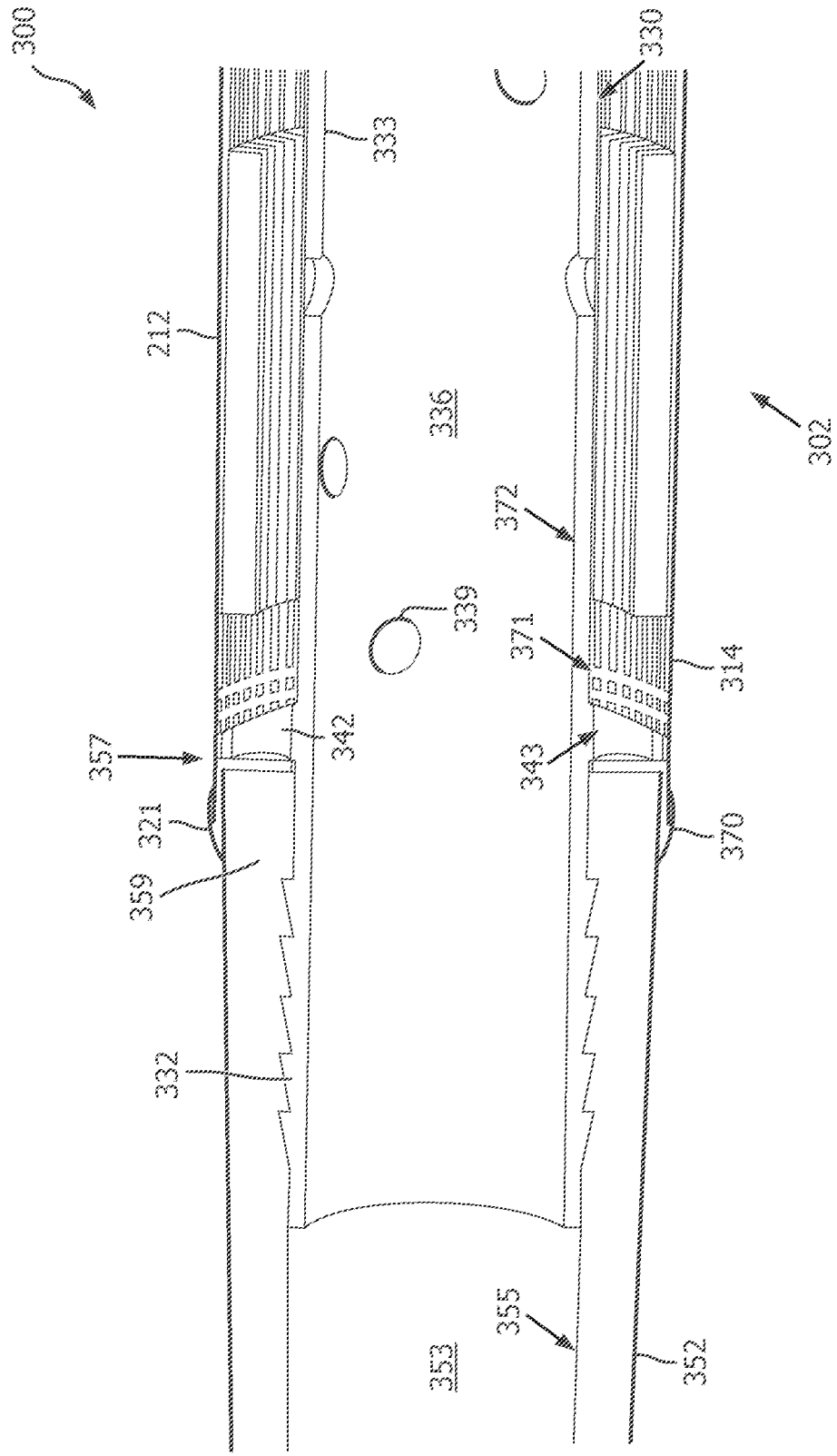
FIG. 10 is a cross-sectional side view illustration of a distal portion of an intravascular device, according to aspects of the present disclosure.

The support member 330 includes the distal flange 332. In various embodiments, the inner diameter and/or outer diameter of the distal flange 332 may be larger than, smaller than, and/or equal to the inner diameter and/or outer diameter of the central portion 333. In an exemplary embodiment, the inner and outer diameters of the distal flange 332 are substantially equal to the inner and outer diameters of the body portion 333. The distal flange 332 may be sized and shaped to facilitate coupling with the distal member 352. In that regard, the distal flange 332 may have cross-sectional profile that is straight/linear, tapered, spiral groove-shaped, screw thread-shaped, buttress thread-shaped, and/or otherwise suitably shaped, including the shapes described in U.S. Provisional App. No. 62/315,395, filed Mar. 30, 2016, the entirety of which is hereby incorporated by reference herein. As shown in FIG. 10, the distal flange 332 engages an inner surface 355 of a lumen 353 of the distal member 352 when the distal member 352 is positioned around the distal flange. The spiral groove or buttress thread shape of the distal flange 332 in the illustrated embodiment advantageously enhances adhesion and/or grip by increasing the surface area of contact between the support member 330 and the distal member 352. This advantageously results in higher pull strength values required to separate the support member 330 and the distal member 352. In some embodiments, the adhesive 370 may be positioned the flex 314, the support member 330, and/or the distal member 352 to support the coupling.

Figure 9:
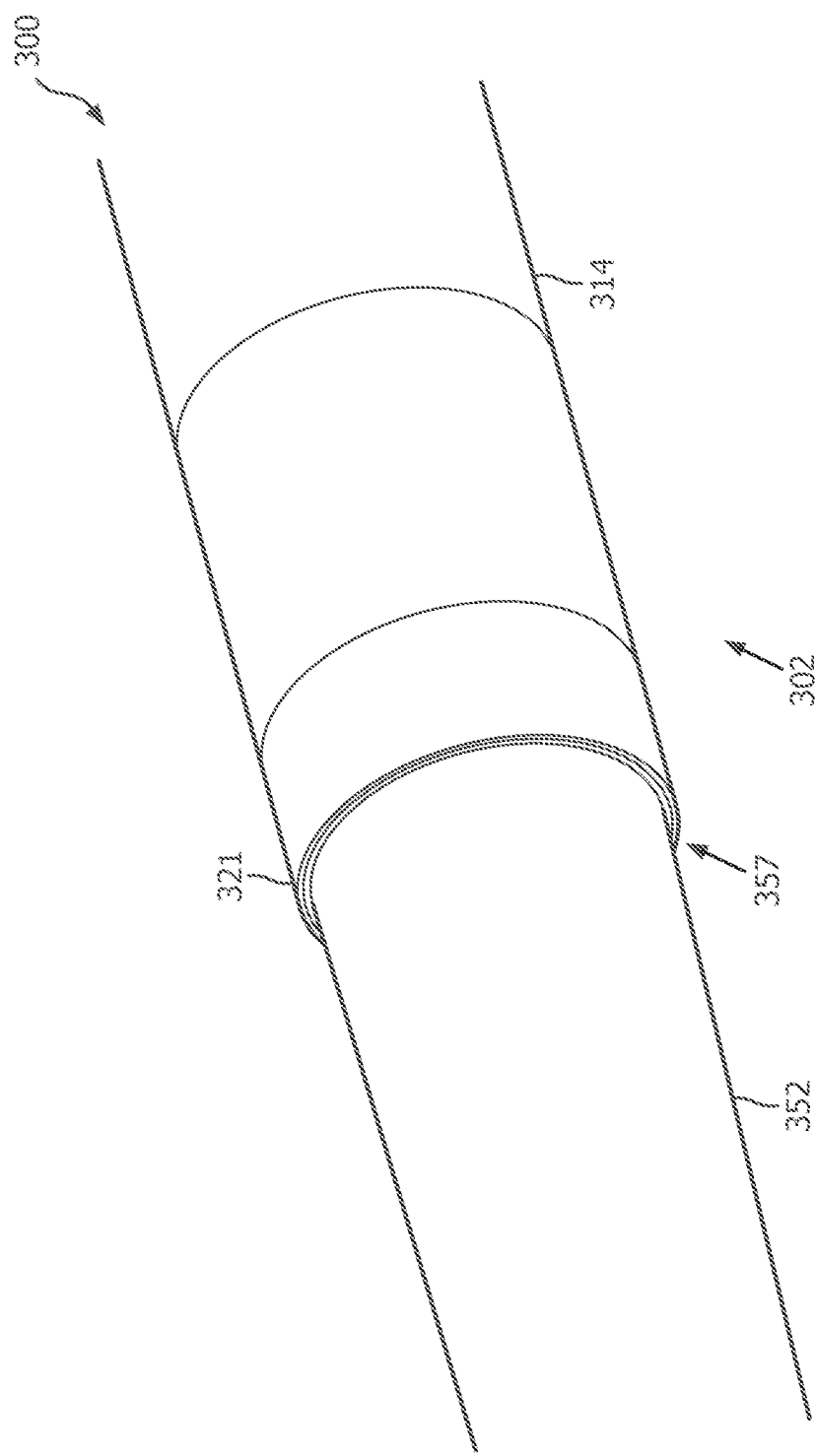
FIG. 9 is a perspective view illustration of a distal portion of an intravascular device, according to aspects of the present disclosure.
Figure 11:
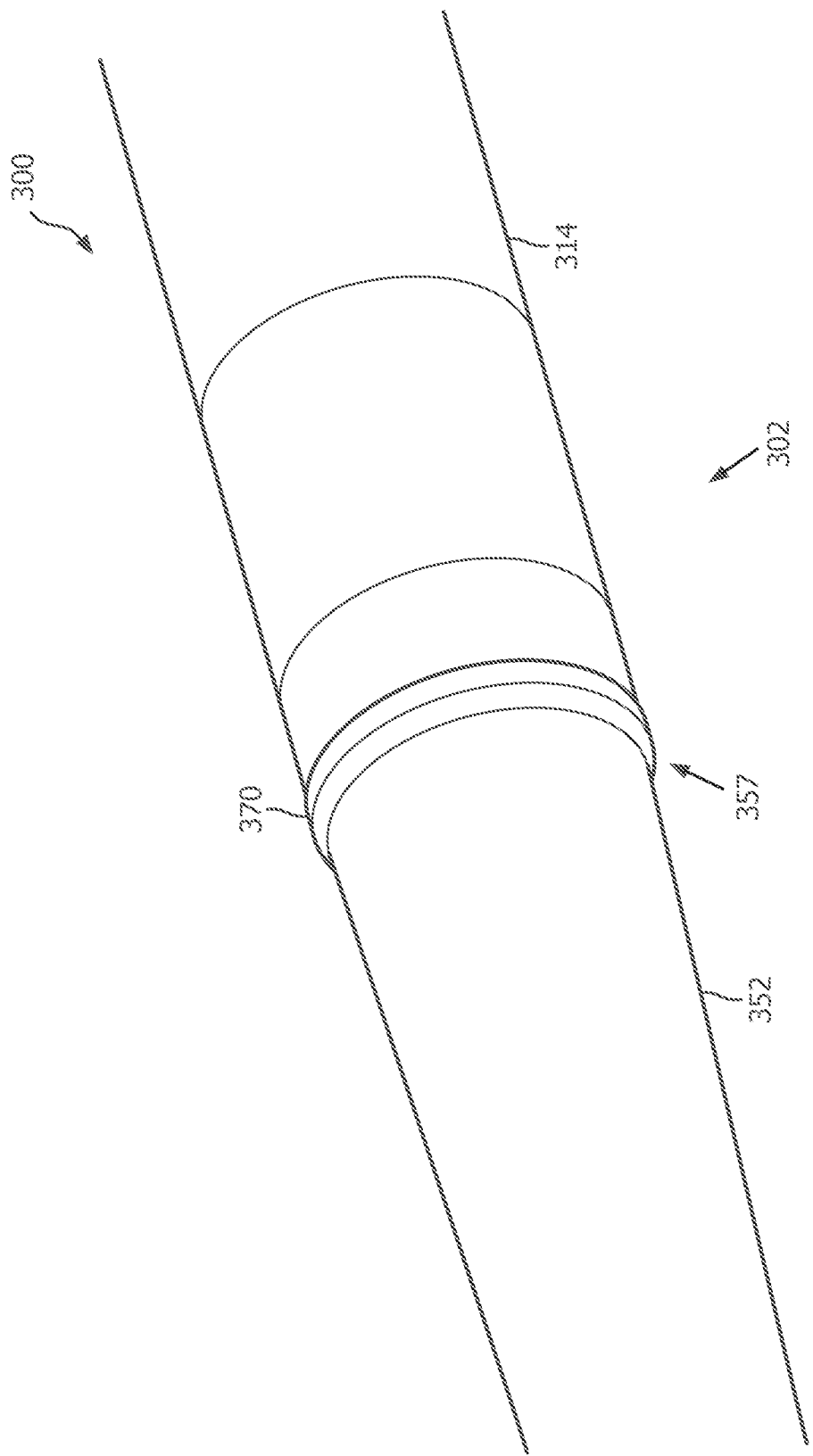
FIG. 11 is a perspective view illustration of a distal portion of an intravascular device, according to aspects of the present disclosure.

FIGS. 9, 10, and 11 illustrate an embodiment of the distal portion of the intravascular device 300 where the flex circuit 314, the support member 330, and/or the distal member 352 are mechanically coupled to one another. FIGS. 9 and 11 are perspective view illustrations of the distal portion of the intravascular device 300, including the imaging assembly 302. FIG. 9 shows a relatively earlier stage of the assembly process for the intravascular device 300, while FIG. 11 shows a relatively later stage. FIG. 10 is a cross-sectional side view illustration of the intravascular device 300, including the imaging assembly 302.

As shown in FIGS. 9 and 10, a distal portion 321 of the flex circuit 314 overlaps a proximal portion 359 of the distal member 352 to form a lap joint 357. Conventional intravascular devices utilized butt joints encapsulated by a fillet that undesirably increases the outer diameter of the intravascular device. The lap joint 357 may be advantageously implemented with adhesive 370 to minimize the outer diameter, such as to achieve a 3F or smaller outer diameter for the intravascular device 300. When the intravascular device 300 is assembled, the proximal portion 359 of the distal member 352 can be coated with the adhesive 370, and the distal member 352 can be moved proximally and slide under distal portion 321 of the flex circuit 314. The adhesive 370 mechanically affixes one or more of the distal member 352, the support member 330, and/or the flex circuit 314 to one another. The distal member 352 can be slide proximally over and around the distal flange 352 such that the distal member 352 abuts distal stand 352. As illustrated in FIG. 11, the adhesive 370 can also be applied around the joint 357. The joint 357 advantageously creates and maintains a hermetic seal for the flex circuit 314. In some embodiments, the lap joint 357 can be formed when the proximal portion 359 of the distal member 352 overlaps the distal portion 321 of the flex circuit 314.

Referring again to FIG. 8, the support member 330 includes a proximal flange 334. The proximal flange 334 may be sized and shaped to facilitate coupling to one or more proximal members 354, 356. In various embodiments, the inner and/or outer diameter of the proximal flange 334 may be larger than, smaller than, and/or equal to the inner and/or outer diameter of the central portion 333. In an exemplary embodiment, the inner and outer diameters of the proximal flange 334 are larger than the inner and outer diameters of the central portion 333. The proximal flange 334 includes a plurality of cavities 341. As described herein, the cavities 341 can facilities adhesion between the proximal members 354, 356, the flex circuit 314, and/or the support member 330 with the adhesive 370.

Figure 14:
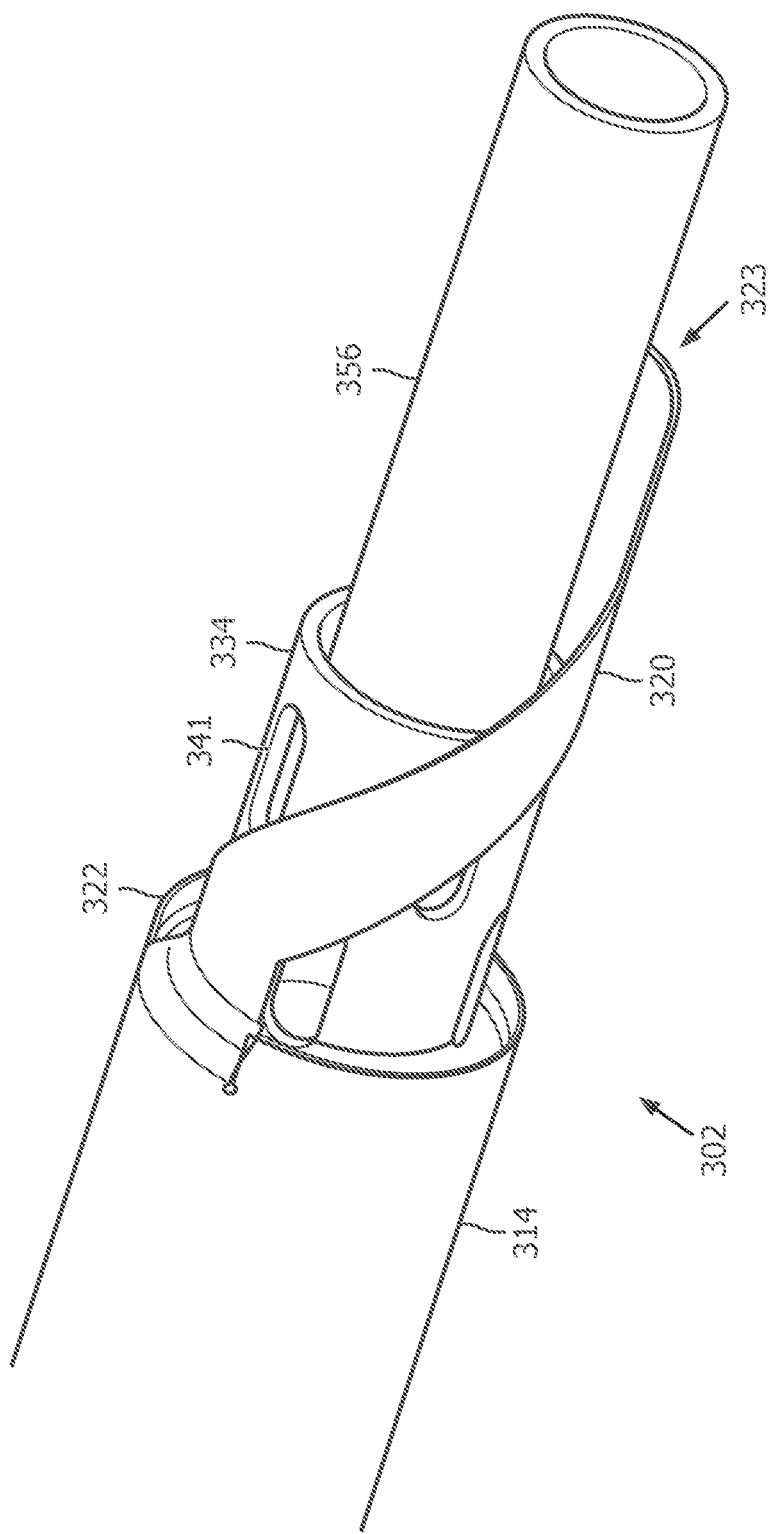
FIG. 14 is a perspective view illustration of an intravascular device, including a distal portion of an imaging assembly, according to aspects of the present disclosure.
Figure 15:
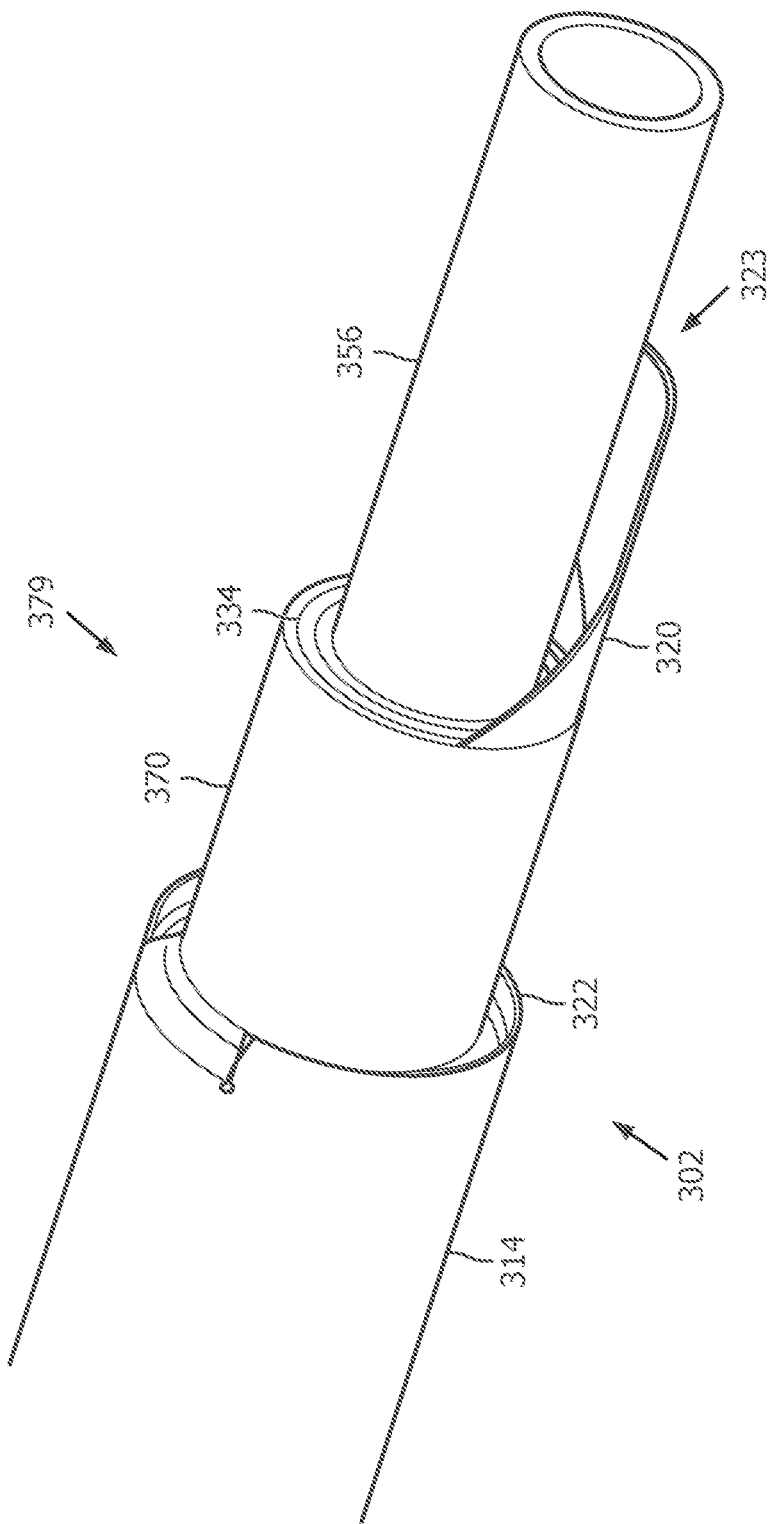
FIG. 15 is a perspective view illustration of an intravascular device, including a distal portion of an imaging assembly, according to aspects of the present disclosure.
Figure 16:
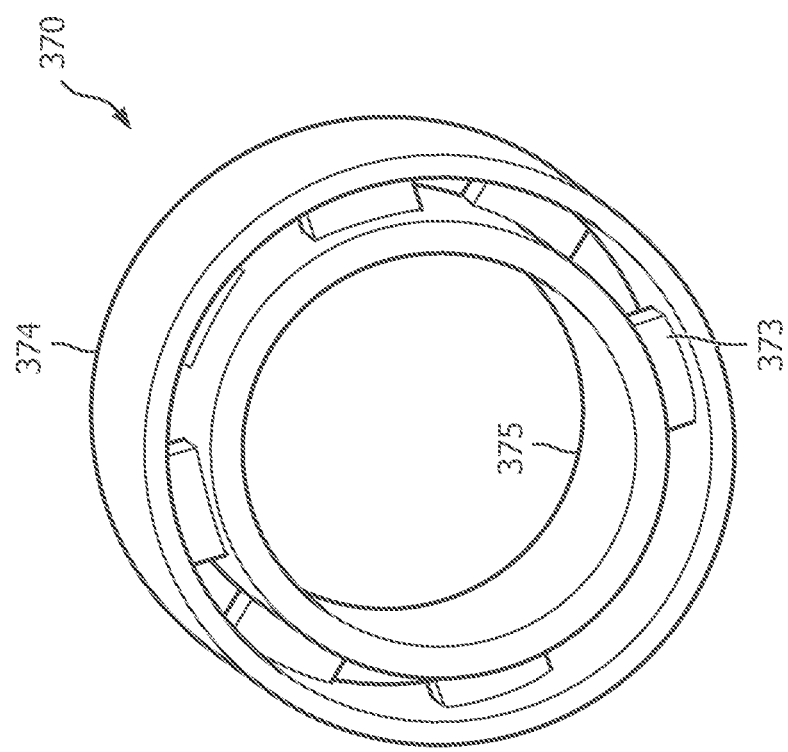
FIG. 16 is a perspective view illustration of adhesive within an intravascular device, absent the components surrounding the adhesive, according to aspects of the present disclosure.

FIGS. 12 and 14-19 illustrate various steps in assembly of the intravascular device 300. In particular, FIGS. 12 and 14-19 show components of the intravascular device 300 at a proximal portion of the imaging assembly 302. FIGS. 12, 14, 15, 18, and 19 are perspective view illustrations of the imaging assembly 302. FIG. 16 is cross-sectional side view illustration of the imaging assembly 302.

The flex circuit 314 includes a conductor interface 320. The conductor interface 320 extends proximally from a proximal portion 322 of the flex circuit 314. One or more conductors 218 of the cable 112 (FIGS. 1 and 2) are electrically coupled to the conductor interface 320. For example, the conductors 218 can be soldered at a proximal portion 323 of the conductor interface 320. By electrically coupling the conductors 218 at the distal portion 323 of the conductor interface 320, the conductors 218 can be soldered at a location spaced from the electronic components in the main body of the flex circuit 414. This may advantageously minimize the outer diameter of the imaging assembly 302 and the intravascular device 300 because the thickness associated with soldering the conductors is moved away from the flex circuit 314. The conductor interface 320 includes conductive traces that are in electrical communication with the flex circuit 314. Electrically coupling the conductors 218 to the conductor interface 320 thus facilitates exchange of electrical signals between the conductors 218, the controllers 206A, 206B, and/or the transducers 212 (FIGS. 2 and 6). The conductor interface 320 extends at an oblique angle relative to a main body of the flex circuit 314. The main body of the flex circuit 314 can collectively describe the transducer region 310, the controller region 308, and the transition region 310.

Figure 13:
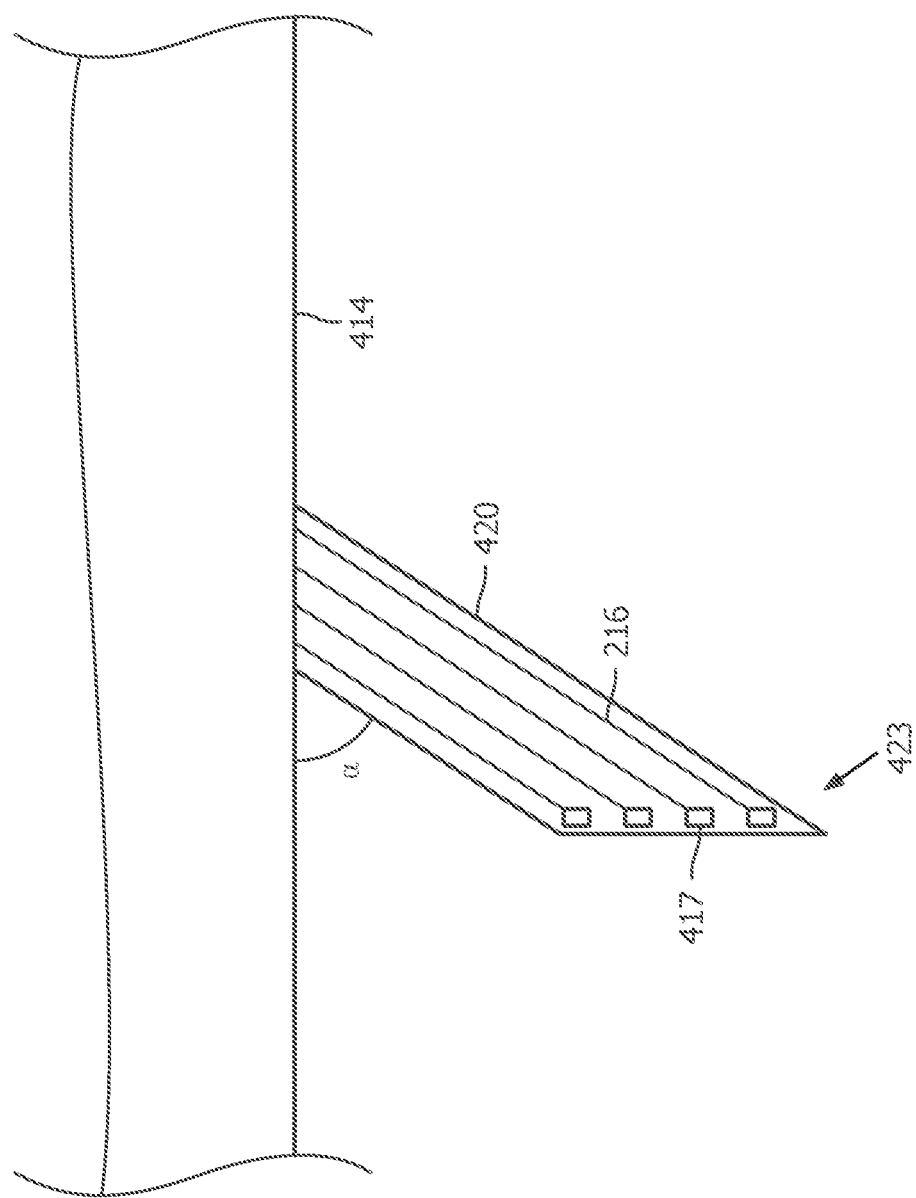
FIG. 13 is a diagrammatic schematic top view of a flex circuit including a conductor interface, according to aspects of the present disclosure.

FIG. 13 is a diagrammatic schematic top view of a flex circuit 414 and a conductor interface 420. The conductor interface 420 forms an oblique angle α with respect to the main body of the flex circuit 414. The oblique angle α may be between approximately 0° and approximately 89° in some embodiments. The oblique angle may be between approximately 91° and approximately 179° in some embodiments. The proximal portion 423 includes conductive pads 417 where the conductors 218 are soldered. The conductive pads 417 are in electrical communication with the conductive traces 215, which are, in turn, in electrical communication with the electronic components of the flex circuit 414.

Figure 12:
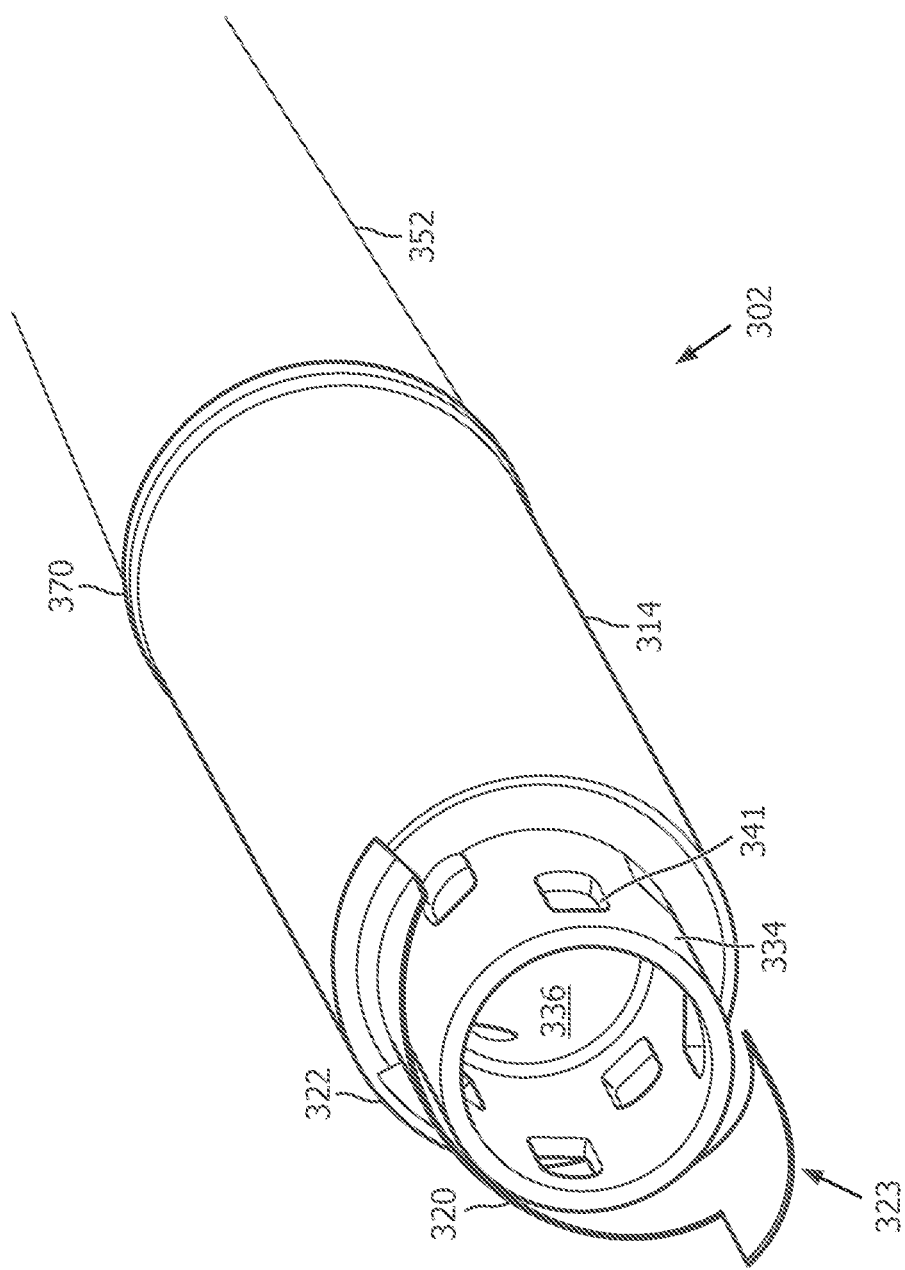
FIG. 12 is a perspective view illustration of an intravascular device, including a distal portion of an imaging assembly, according to aspects of the present disclosure.

As shown in FIGS. 12 and 14, the conductor interface 320 can be positioned around the proximal flange 334. For example, the conductor interface 320 can be wrapped in a spiral or helical configuration around the proximal flange 334. The conductor interface 320 can be wound around the proximal flange 334 any suitable number of times, depending on the length of the conductor interface 320. In other embodiments, the conductor interface 320 can extend proximally from the main body of the flex circuit in a different manner, such as a linear/straight configuration, a curved configuration, etc.

The flex circuit 314, the support member 330, and/or the proximal members 354, 356 are coupled with the adhesive 370 at the proximal joint 379. FIG. 14 illustrates that the inner proximal member 356 can be inserted into and received within the proximal flange 334. The conductor interface 320 may be wrapped in a spiral configuration around both the proximal flange 334 and the inner member 356 in some embodiments. In such embodiments, the conductors 218 can extend along the length of the intravascular device 300 within a lumen of the outer member 354, between the inner member 356 and the outer member 354.

Figure 17:
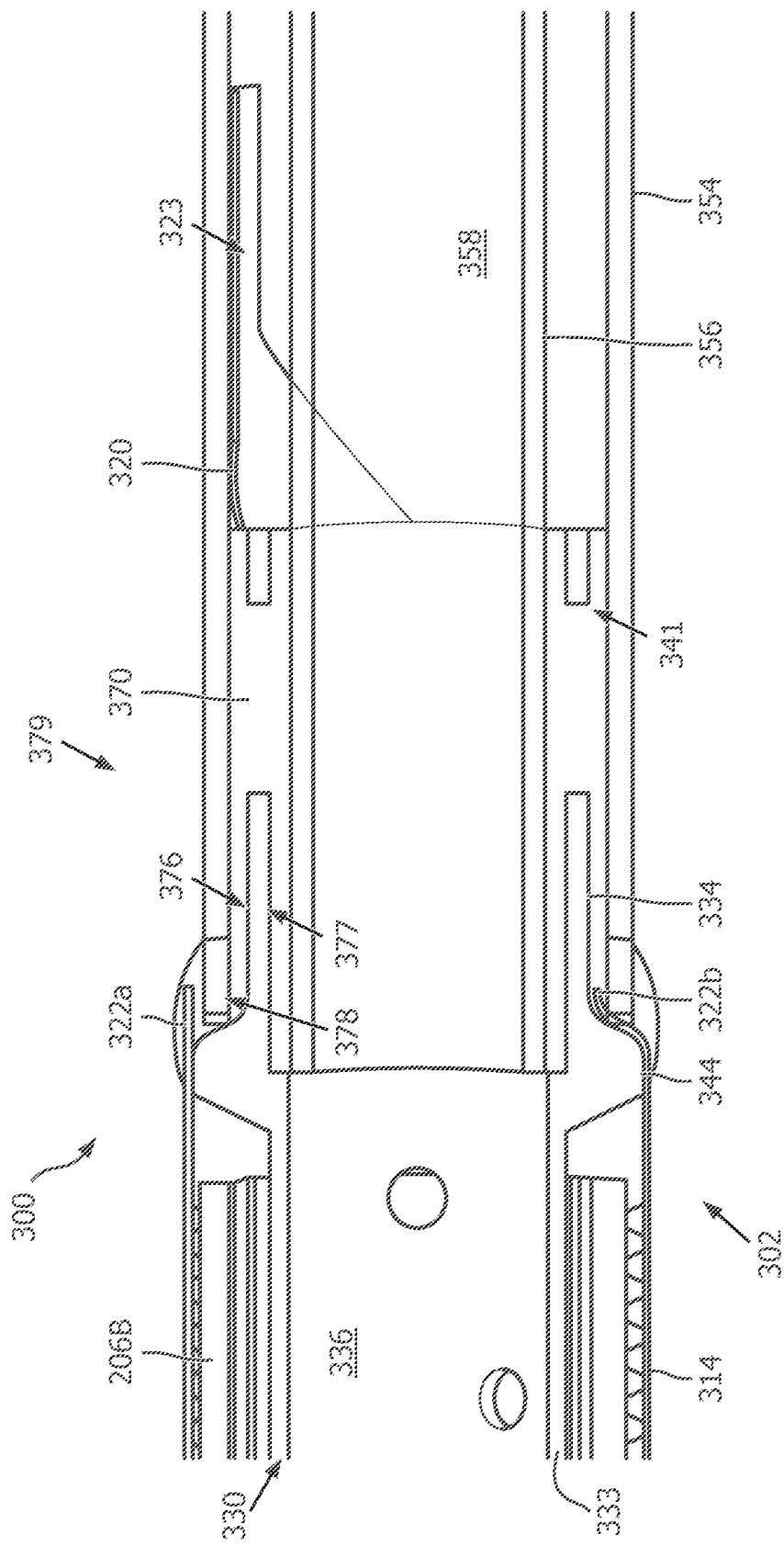
FIG. 17 is a cross-sectional side view illustration of an intravascular device, including a distal portion of an imaging assembly, according to aspects of the present disclosure.

The adhesive 370 is applied onto and around the proximal flange 334, as illustrated in FIG. 15-17. The adhesive 370 flows through the cavities 341 of the proximal flange 334 so that the adhesive 370 covers surfaces of the inner member 356 and the support member 330. The cavities 341 are longitudinally and/or circumferentially distributed on the proximal flange 334. Each of the cavities 341 extends radially from an outer surface 376 of the proximal flange 334 through an inner wall 377 of the lumen 336. As described above, in some embodiments, the inner diameter of the lumen 336 may be larger in proximal flange than in the central portion 333. The cavities 341 establish fluid communication between spaces of the intravascular device above/outside (e.g., between the outer member 354 and the proximal flange 334) and below/inside (e.g., within the lumen 336, between the proximal flange 334 and the inner member 356) of the proximal flange 334. In that regard, the cavities 341 may be distributed and/or spaced from one another such that the adhesive 370 evenly coats the support member 330, the flex circuit 314, and/or the proximal member 354, 356. The cavities 341 may have any suitable shape, including oblong (as shown), circle, polygon, ellipse, etc. The cavities 341 advantageously allow for light to travel to penetrate the proximal flange 334 and cure the adhesive 370.

FIG. 16 illustrates a stylized shape that the adhesive 370 assumes when the proximal portion of the imaging assembly 302 is coated with the adhesive 370. The structural components of the intravascular device 300 are not visible in FIG. 15. The pillars 373 of the adhesive 370 extend within the cavities 341 of the proximal flange 334. The pillars 373 are formed between an outer circumference 374 and an inner circumference 375. The inner circumference 375 establishes adhesive contact between the proximal flange 334 and the inner member 356. The outer circumference 374 establishes adhesive contact between the proximal flange 334 and the outer member 354. The pillars 373 extending through the cavities 341 establishes continuity between the outer and inner circumferences 374, 375 and strengthens the bond between the support member 330 and the proximal members 354, 356.

Figure 18:
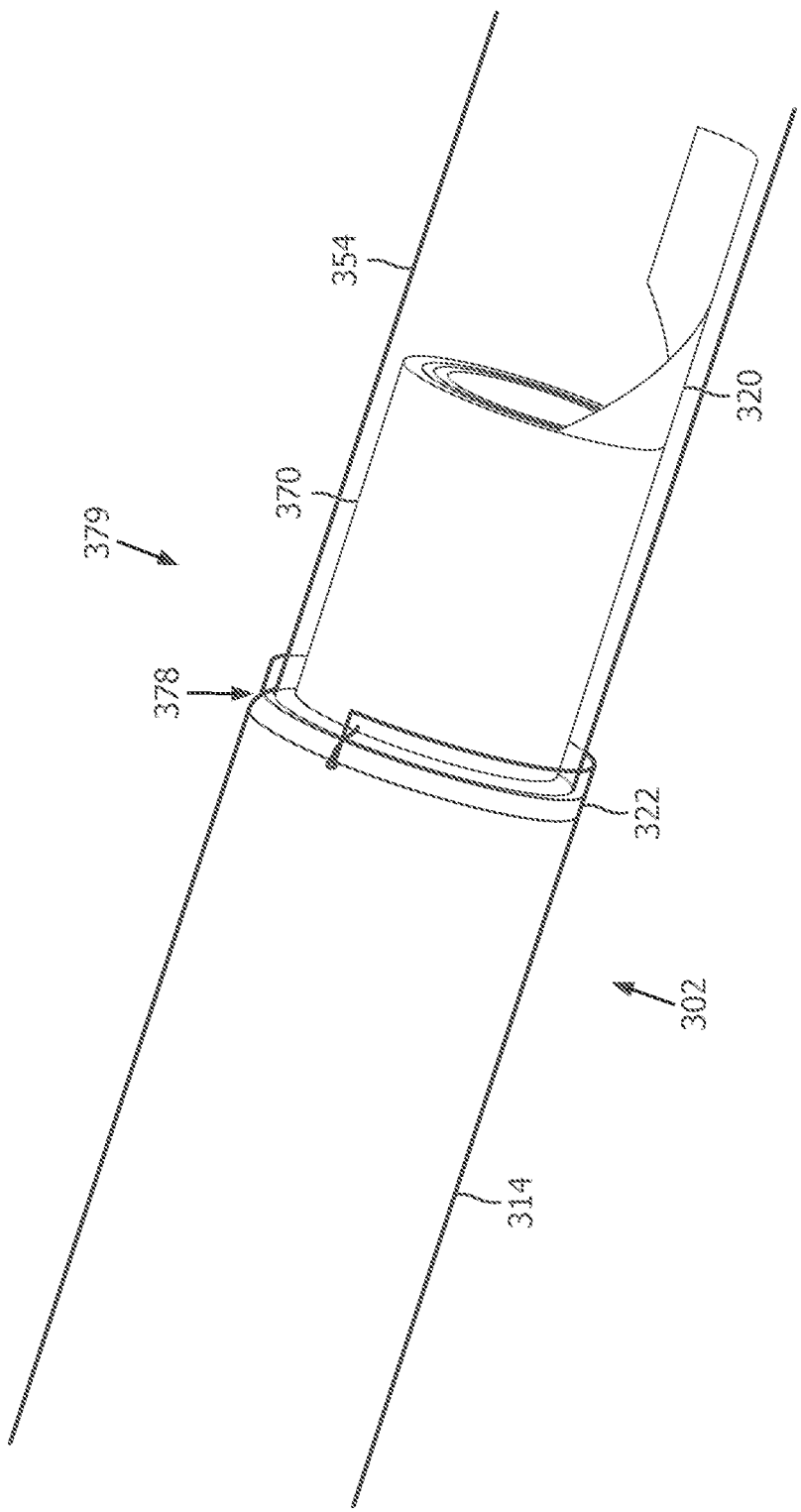
FIG. 18 is a perspective view illustration of an intravascular device, including a distal portion of an imaging assembly, according to aspects of the present disclosure.
Figure 19:
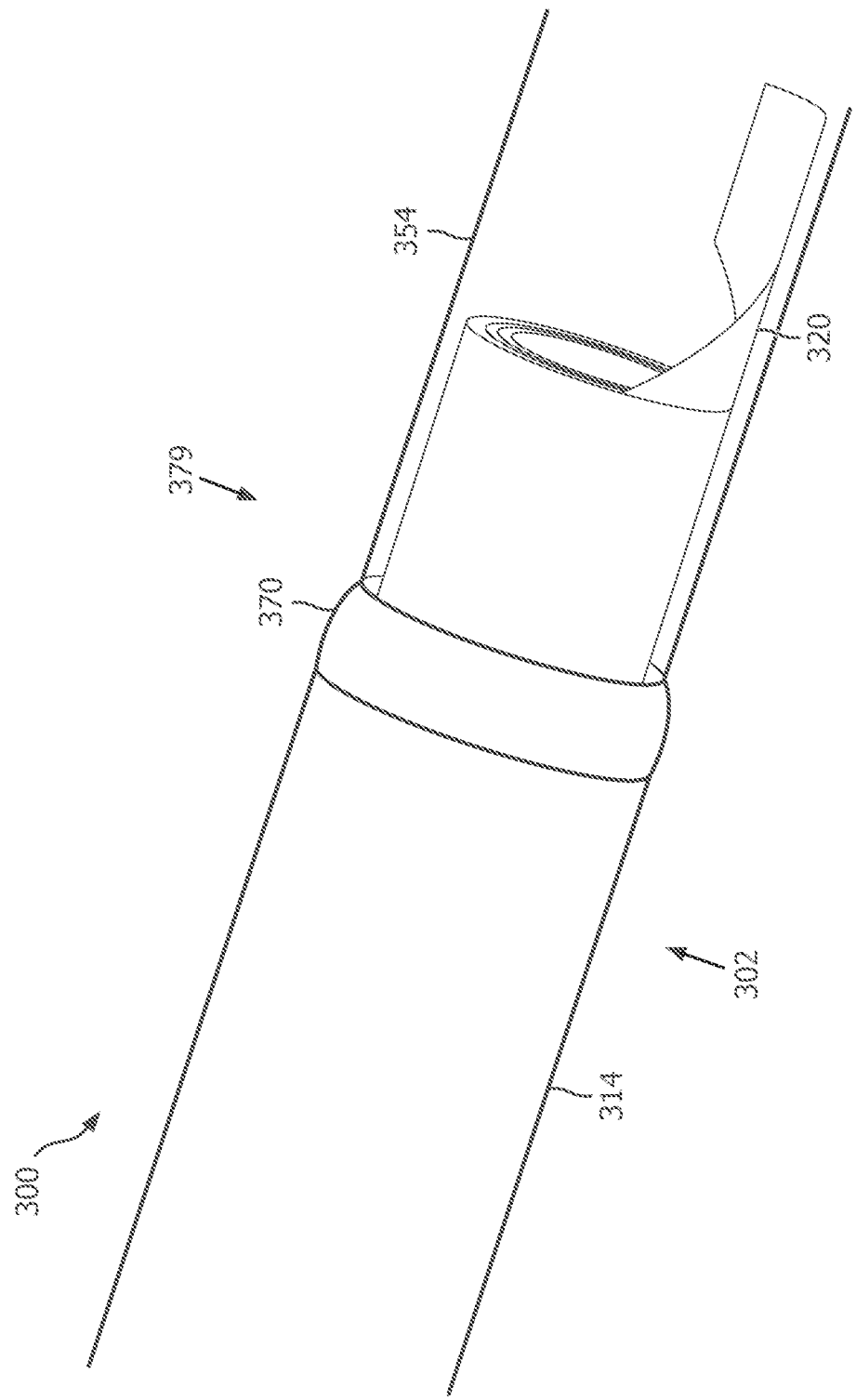
FIG. 19 is a perspective view illustration of an intravascular device, including a distal portion of an imaging assembly, according to aspects of the present disclosure.

As shown in FIGS. 17-19, the outer member 354 can be moved distally over and around the proximal flange 334 and the conductor interface 320 until the outer member 354 abuts the proximal stand 344. The proximal joint 379 can be a lap joint, which can advantageously seal the flex circuit 314 using the adhesive 370. For example, a distal portion 378 can overlap a proximal portion 322b in some embodiments. In such embodiments, the proximal portion 322b may be bent and secured to the proximal flange 334, allowing the outer member 354 to slide over the proximal portion 322b. In other embodiments, a proximal portion 322a of the flex circuit 314 overlaps the outer member 354. In such embodiments, the distal portion 378 of the outer member may be slid underneath the proximal portion 322a. The distal portion 378 and/or the proximal portion 322a, 322b may be coated with the adhesive 370. As illustrated in FIG. 19, the adhesive 370 can also be applied around the joint 379.

Various embodiments of an intravascular device and/or imaging assembly can include features described in U.S. Provisional App. No. 62/315,395, filed on Mar. 30, 2016, U.S. Provisional App. No. 62/315,406, filed on Mar. 30, 2016, U.S. Provisional App. No. 62/315,421, filed on Mar. 30, 2016, and U.S. Provisional App. No. 62/315,416, filed on Mar. 30, 2016, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device comprising:
a flexible elongate member sized and shaped for insertion into a vessel of a patient, the flexible elongate member comprising a proximal portion and a distal portion; and
an imaging assembly disposed at the distal portion of the flexible elongate member, wherein the imaging assembly comprises:
a flex circuit;
a support member, wherein the flex circuit is disposed around the support member, wherein the support member comprises a proximal portion and a distal portion, wherein the proximal portion of the support member comprises a plurality of cavities; and
an adhesive configured to couple the flexible elongate member and the support member, wherein the adhesive extends through the plurality of cavities such that the adhesive contacts the distal portion of the flexible elongate member and the proximal portion of the support member.

2. The device of claim 1,
wherein the proximal portion of the support member comprises an inner surface and an outer surface,
wherein the plurality of cavities extend radially between the inner surface and the outer surface.

3. The device of claim 2, wherein the adhesive is disposed on the inner surface and the outer surface.

4. The device of claim 1, wherein the plurality of cavities are distributed in at least one of a longitudinal manner or a circumferential manner.

5. The device of claim 1,
wherein the support member comprises a proximal stand,
wherein the proximal portion of the support member comprises a portion of the support member that is proximal of the proximal stand,
wherein an outer diameter of the proximal stand is larger than an outer diameter of the proximal portion of the support member, and
wherein the flex circuit is disposed around the support member such that the flex circuit is in contact with the proximal stand.

6. The device of claim 1,
wherein the flexible elongate member comprises an inner member received within the proximal portion of the support member,
wherein the adhesive contacts the inner member.

7. The device of claim 6,
wherein the adhesive is disposed between proximal portion of the support member and the inner member.

8. The device of claim 1,
wherein the flexible elongate member comprises an outer member positioned around the proximal portion of the support member,
wherein the adhesive contacts the outer member.

9. The device of claim 8,
wherein the adhesive is disposed between proximal portion of the support member and the outer member.

10. The device of claim 1,
wherein the flexible elongate member comprises:
an inner member received within the proximal portion of the support member; and
an outer member positioned around the proximal portion of the support member, wherein the adhesive contacts the inner member and the outer member.

11. The device of claim 10,
wherein the adhesive forms a shape comprising:
an inner circumference extending between the proximal portion of the support member and the inner member;
an outer circumference extending between the proximal portion of the support member and the outer member; and
a plurality of pillars extending radially between the inner circumference and the outer circumference, and
wherein the plurality of pillars correspond to portions of the adhesive extending through the plurality of cavities.

12. The device of claim 1, wherein the flex circuit comprise a plurality of ultrasound transducers and a plurality of integrated circuits.

* * * * *